United States Patent [19]

Lassen et al.

[11] Patent Number: 4,593,036

[45] Date of Patent: Jun. 3, 1986

[54] (−)-TRANS-4-(4-FLUOROPHENYL)-3-[(4-METHOXYPHENOXY)METHYL]-1-METHYLPIPERIDINE USEFUL AS 5-HT POTENTIATOR

[75] Inventors: Jorgen B. Lassen, Glostrup; Jorgen A. Christensen, Virum; Erling N. Petersen, Glostrup; John B. Hansen, Lyngby, all of Denmark

[73] Assignee: A/S Ferrosan, Soborg, Denmark

[21] Appl. No.: 577,845

[22] Filed: Feb. 7, 1984

[51] Int. Cl.[4] .................. C07D 211/22; A61K 31/445
[52] U.S. Cl. ..................................... 514/317; 546/236
[58] Field of Search ........................ 546/236; 424/267; 514/317

[56] References Cited

U.S. PATENT DOCUMENTS 3,912,743  10/1975  Christensen et al. ............... 546/236
4,007,196  2/1977  Christensen et al. ............... 546/236

OTHER PUBLICATIONS

European Journal of Pharmacology, 43, (1977), 209–215.

Primary Examiner—Norma S. Milestone
Attorney, Agent, or Firm—Gordon W. Hueschen

[57] ABSTRACT

The compound (−)-trans-4-(4-florophenyl)-3-[(4-methoxyphenoxy)methyl]-1-methylpiperidine and pharmaceutically-acceptable acid addition salts thereof, pharmaceutical compositions thereof, and their use in potentiating the 5-hydroxytryptamine(5-HT) of a subject in need thereof, for the alleviation of any of various physiological abnormalities, are disclosed.

8 Claims, No Drawings

(−)-TRANS-4-(4-FLUOROPHENYL)-3-[(4-METHOXYPHENOXY)METHYL]-1-METHYL-PIPERIDINE USEFUL AS 5-HT POTENTIATOR

BACKGROUND OF INVENTION

1. Field of Invention

Fluorophenyl[methoxyphenoxymethyl]piperidine compounds and acid addition salts thereof, pharmaceutical compositions thereof, and method-of-treating therewith. Serotonin or 5-hydroxytryptamine (5-HT) potentiating compounds and their employment for indications caused by or resulting or arising from a disturbance of the serotonin or 5-HT system.

2. Prior Art

The most relevant prior art is to be found in U.S. Pat. Nos. 3,912,743 and 4,007,196, respectively issued Oct. 14, 1975 and Feb. 8, 1977, in which the same general type of compound and activity is disclosed without, however, any suggestion of the particular and specific compounds involved according to the present invention, much less of the particular and specific "subject matter as a whole", including not only their chemical structures but also the pharmacological properties thereof, which "subject matter as a whole" according to the present invention has been found to be both advantageous and unobvious from the standpoint of one skilled in the art.

OBJECTS

It is an object of the present invention to provide the novel compound (−)-trans-4-(4-fluorophenyl)-3-[(4-methoxyphenoxy)methyl]-1-methylpiperidine and pharmaceutically-acceptable acid addition salts thereof, which are useful as 5-HT potentiators and in the treatment or alleviation of ailments and/or conditions caused by or resulting or arising from disturbance of the 5-HT system, a process for producing the same, pharmaceutical compositions thereof, intermediates therefor, and a method of treating therewith. Additional objects will become apparent hereinafter, and still others will be obvious to one skilled in the art.

SUMMARY OF THE INVENTION

The invention, in summary, comprises the following: A compound selected from the group consisting of (−)-trans-4-(4-fluorophenyl)-3-[(4-methoxyphenoxy)-methyl]-1-methylpiperidine and a pharmaceutically-acceptable acid addition salt thereof; such compound which is (−)-trans-4-(4-fluorophenyl)-3-[(4-methoxyphenoxy)methyl]-1-methylpiperidine hydrochloride; a pharmaceutical composition suitable for use in 5-HT potentiation comprising an effective 5-HT potentiating amount of (−)-trans-4-(4-fluorophenyl)-3-[(4-methoxyphenoxy)methyl]-1-methylpiperidine or a pharmaceutically-acceptable acid addition salt thereof, and especially (−)-trans-4-(4-fluorophenyl)-3-[(4-methoxyphenoxy)methyl]-1-methylpiperidine hydrochloride; a method of potentiating the 5-HT of a subject in need thereof comprising the step of administering to the subject an effective 5-HT potentiating amount of (−)-trans-4-(4-fluorophenyl)-3-[(4-methoxyphenoxy)methyl]-1-methylpiperidine or a pharmaceutically-acceptable acid addition salt thereof, and especially (−)-trans-4-(4-fluorophenyl)-3-[(4-methoxyphenoxy)methyl]-1-methylpiperidine hydrochloride; and such a method wherein the 5-HT potentiating compound is administered in the form of a pharmaceutical composition containing also a pharmaceutically-acceptable carrier or diluent.

IDENTITY

The free basic compound of the present invention has the formula

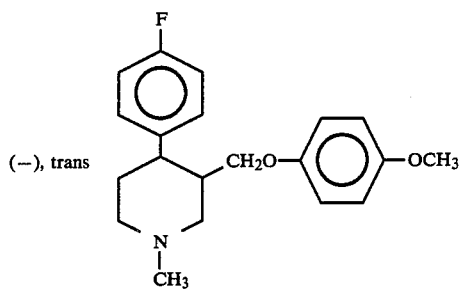

(−), trans and suitable pharmaceutically-acceptable acid addition salts thereof include addition salts with both inorganic and organic acids, representatively the hydrochloride, hydrobromide, sulfate, phosphate, acetate, fumarate, maleate, citrate, lactate, tartrate, or similar pharmaceutically-acceptable inorganic or organic acid addition salt. Such acid addition salts are ordinarily formed by reacting the free base with an equivalent amount or excess of the selected acid, frequently and suitably by admixture in the presence of a neutral solvent, from which the addition salt may be precipitated or recovered in other conventional manner, e.g., by evaporation. Administration of a compound of the invention is preferably in the form of a pharmaceutically-acceptable water-soluble acid addition salt thereof, and orally, rectally, or parenterally in the form of a pharmaceutical composition where it is present together with a pharmaceutically-acceptable liquid or solid carrier or diluent. The hydrochloride (FG 8033) has a melting point of 178°–179° C. and an $[\alpha]_D^{20}$ of −75° (c=5 in 96% ethanol).

PREPARATION

Preparation of the compounds of the present invention from known starting material is effected according to the following specific Examples, pursuant to the following reaction sequence

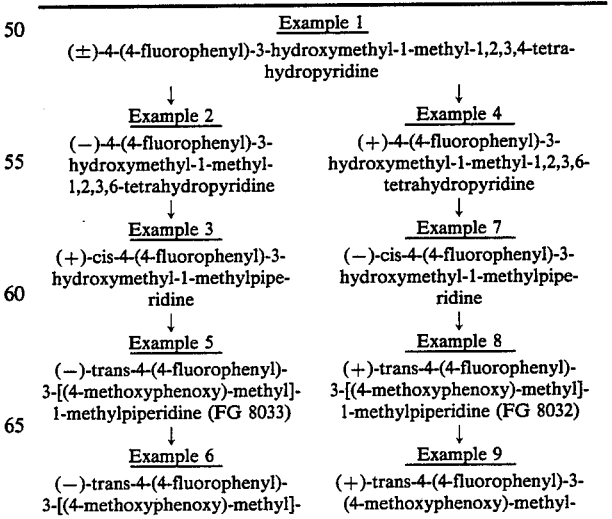

| piperidine (FG 7080) | piperidine (FG 8035) |

The compound of the invention will be recognized as the product of example 5 (FG 8033).

The comparative racemic N—Me; 4-fluoro compound (FG 98-I) of Table I can be isolated from the mother liquors in Examples 5 and 8 inasmuch as the reductions there involved are not totally specific.

The remaining comparative compounds in Table I are synthesized according to the procedure of U.S. Pat. No. 3,912,743 or 4,007,196, as indicated in the Table.

PHARMACEUTICAL COMPOSITIONS

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective 5-HT potentiating (or 5-HT uptake-inhibiting) amount of the active ingredient commensurate with the intended daily dosage range to be employed. Tablets containing ten (10) milligrams of active ingredient or, more broadly, ten (10) to thirty (30) milligrams, per tablet, are accordingly suitable representative unit dosage forms.

METHOD OF TREATING

Due to their high degree of 5-HT potentiating (or 5-HT uptake-inhibiting) activity and their low toxicity, together presenting a most favorable therapeutic index, the compounds of the invention may be administered to a subject, e.g., a living animal body, in need of the potentiation of serotonin (5-HT) for the alleviation, treatment, or amelioration of an indication which is sensitive to a change in the serotonin balance, whether it be central or peripheral nervous system serotonin balance or blood constituent serotonin balance, for example the blood platelet serotonin balance, representatively of an indication set forth in items A through N in the following, preferably in the form of an acid addition salt thereof, concurrently, simultaneously, or together with a pharmaceutically-acceptable carrier or diluent, especially and preferably in the form of a pharmaceutical composition thereof, whether by oral, rectal, or parenteral (including subcutaneous) route, in an effective serotonin (5-HT) potentiating (or 5-HT uptake-inhibiting) amount. Suitable dosage ranges are 1–200 milligrams daily, preferably 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

DETAILED DESCRIPTION OF THE INVENTION

The following Examples are given by way of illustration only.

EXAMPLE 1

(±)-4-(4-fluorophenyl)-3-hydroxymethyl-1-methyl-1,2,3,6-tetrahydropyridine

Dissolve 3.8 kg of methylamine hydrochloride in 16.1 l of 40% w/w formaldehyde solution and heat to about 70° C. Add 7.0 l of 4-fluoro-α-methylstyrene (known commercially-available compound; usual source Aldrich or Janssen, for example) portionwise to the stirred mixture. The mixture is refluxed for four (4) hours. After cooling the mixture is extracted with 3 l of toluene whereafter 4.2 of concentrated hydrochloric acid is added to the aqueous reaction mixture which is then refluxed for about 18 hours. 12.1 l of aqueous ammonia solution (d=0.88) is then added portionwise and material precipitating between pH 6.4 and pH 9.2 is extracted into 16 l of toluene. The toluene solution is then extracted portionwise with dilute (0.5N) hydrochloric acid (64.5 l) and extracts between pH 6.5 and pH 7.25 are combined. Finally, 3 l of aqueous ammonia solution (d=0.88) is added to these combined extracts and the product which precipitates is extracted into 10 l of toluene, which is then dried over potassium carbonate. Evaporation of the dried toluene solution under reduced pressure gives 5.7 kg of crude (±)-4-(4-fluorophenyl)-3-hydroxymethyl-1-methyl-1,2,3,6-tetrahydropyridine.

EXAMPLE 2

(−)-4-(4-fluorophenyl)-3-hydroxymethyl-1-methyl-1,2,3,6-tetrahydropyridine

Dissolve 1765 g of (−)-dibenzoyltartaric acid hydrate in 4.5 l of methanol and dissolve 1000 g of (±)-4-(4-fluorophenyl)-3-hydroxymethyl-1-methyl-1,2,3,6-tetrahydropyridine in 500 ml of methanol. The combined solutions are cooled to 0° C. and left to stand overnight.

The precipitated (−)-4-(4-fluorophenyl)-3-hydroxymethyl-1-methyl-1,2,3,6-tetrahydropyridine dibenzoyltartrate is isolated. The yield is 946 g; M.p. 155°–156° C.; $[\alpha]_D^{20}$ −118 (c=2 in methanol).

Mix and stir 946 g of the dibenzoyltartrate, 1.25 l of toluene, 4.25 l of water, and 0.39 kg of sodium carbonate. The phases are separated. The aqueous phase is extracted successively with one (1) liter and one-half liter of toluene. The combined toluene phases are dried with potassium carbonate, filtered, and evaporated to yield 350 g of (−)-4-(4-fluorophenyl)-3-hydroxymethyl-1-methyl-1,2,3,6-tetrahydropyridine, having an $[\alpha]_D^{20}$ −134.3 (c=5 in methanol).

EXAMPLE 3

(+)-cis-4-(4-fluorphenyl)-3-hydroxymethyl-1-methyl-piperidine

Mix 250 g of (−)-4-(4-fluorophenyl)-3-hydroxymethyl-1-methyl-1,2,3,6-tetrahydropyridine, 550 ml of ethanol, 450 ml of water, and 110 ml of concentrated hydrochloric acid and add five (5) g of Pd-catalyst (5% Pd on charcoal) to the mixture. Reduce the mixture in an autoclave at 40°–45° C. at a pressure of seventy (70) kg/cm². The reduction is terminated after two hours. The hot reaction mixture is filtered and one liter of filtrate is distilled from the mixture under vacuum. Seventy (70) ml of a 50% w/w sodium hydroxide solution and 250 ml of toluene are added to the residue. The solution is cooled and the phases are separated. The aqueous phase is extracted twice with 100 ml of toluene. The combined toluene phases are dried and evaporated to give a residue of 245 g.

The residue is recrystallized from 250 ml of petroleum (b.p. 100°–140° C.) to yield 225 g of (+)-cis-4-(4-fluorophenyl)-3-hydroxymethyl-1-methylpiperidine. Mp. 65°–67° C., $[\alpha]_D^{20}$ 75° (c=5 in methanol).

EXAMPLE 4

(+)-4-(4-fluorophenyl)-3-hydroxymethyl-1-methyl-1,2,3,6-tetrahydropyridine hydrochloride A quantity (1816 g) of mother liquor from Example 2 is evaporated. The residue is dissolved in 600 ml of methanol and 1816 ml of toluene, whereafter 605 g of sodium carbonate in 4.5 l of water is added. After stirring, the phases are separated. The aqueous phase is extracted twice with 900 ml of toluene. The combined toluene phases are dried and evaporated to leave a residue of 650 g.

The residue is dissolved in 880 ml of 4N hydrochloric acid and the solution is evaporated; then 1.2 l of ethanol-toluene (1:2) is added and the solution again evaporated. The residue is recrystallized from 1.5 l of acetone to yield 409.2 g of (+)-4-(4-fluorophenyl)-3-hydroxymethyl-1-methyl-1,2,3,6-tetrahydropyridine hydrochloride. M.p. 165°–170° C., $[\alpha]_D^{20}$ 92° (c=5 in methanol).

EXAMPLE 5

(−)-trans-4-(4-fluorophenyl)-3-[(4-methoxyphenoxy)-methyl]-1-methyl-piperidine (FG 8033)

Twenty grams (20 g) of (+)-cis-4-(4-fluorophenyl)-3-hydroxymethyl-1-methylpiperidine is dissolved in 100 ml of toluene and 22 ml triethylamine and the solution cooled to 0° C. Thirteen (13) ml of benzenesulfonylchloride is added over a period of thirty (30) minutes. The mixture is left overnight. Six (6) g of sodium is dissolved in eighty (80) ml of methanol and the mixture is evaporated. The residue is dissolved in 100 ml of methyl isobutyl carbinol containing 18 g of p-methoxyphenol, the mixture is evaporated, and the residue redissolved in 100 ml of methyl isobutyl carbinol. This mixture is mixed with the above-prepared benzenesulfonic acid ester solution and the triethylamine is distilled off. The mixture is then refluxed for one hour and evaporated. Thirty (30) ml of water is added to the residue and the mixture again evaporated. The residue is partitioned between 100 ml of water and 100 ml of toluene. The aqueous phase is extracted twice with fifty (50) ml portions of toluene. The combined toluene phases are evaporated to give the title compound as the hydrochloride. M.p. of hydrochloride 178°–179° C.; $[\alpha]_D^{20}$ −75° (c=5 in 96% EtOH).

EXAMPLE 6

(−)-trans-4-(4-fluorophenyl)-3-[(4-methoxyphenoxy)-methyl]-piperidine (FG 7080)

Twenty (20) g of the base of Example 5 is dissolved in 95 ml of toluene and the solution cooled to 0° C. Then 9.5 ml of chloroformic acid phenylester in nineteen (19) ml of toluene is added slowly at 4°–6° C. The mixture is left to stand for sixty (60) hours at RT (room temperature). The toluene solution is extracted twice with twenty (20) ml of 2N NaOH and twice with 1N HCl. The toluene phase is dried with potassium carbonate and evaporated. The residue is recrystallized from 99% ethanol to yield sixteen (16) g of product. This product is mixed with 8.6 g of potassium hydroxide and 41.3 ml ethylene glycol monomethyl ether. The mixture is refluxed for two hours, whereafter 42 ml of water and sixty (60) ml of toluene is added. The aqueous phase is extracted twice with 25 ml of toluene. The combined toluene phases are dried with potassium carbonate and evaporated to yield 11.6 g of product. The product is dissolved in forty (40) ml of 1N hydrochloric acid and evaporated, the residue then dissolved in fifty (50) ml of ethanol and again evaporated, and the residue from that evaporation dissolved in twenty (20) ml of 99% ethanol. Ether is added until the product precipitates, and this procedure is repeated once to give a yield of 10.4 g of the title compound as the hydrochloride. M.p. 165°–168° C. $[\alpha]_D^{20}$ −81 (c=5 in 96% ethanol).

EXAMPLE 7

(−)-cis-4-(4-fluorophenyl)-3-hydroxymethyl-1-methylpiperidine hydrochloride

Thirty-five (35) g of (+)-4-(4-fluorophenyl)-3-hydroxymethyl-1-methyl-1,2,3,6-tetrahydropyridine hydrochloride and 5.5 g of Pd-catalyst (5% Pd on charcoal) are mixed in 2900 ml of 99% ethanol. The mixture is reduced at room temperature under one atmosphere of hydrogen pressure over a period of six hours, taking up 3250 ml of hydrogen. The reaction mixture is filtered and the filtrate is evaporated. The residue is washed with ether to give 33.5 g of the title compound. M.p. 158°–159° C.

EXAMPLE 8

(+)-trans-4-(4-fluorophenyl)-3-[(4-methoxyphenoxy)-methyl]-1-methylpiperidine hydrochloride (FG 8032)

First, 31.5 g of (−)-cis-4-(4-fluorophenyl)-3-hydroxymethyl-1-methylpiperidine hydrochloride is partitioned between basic water and toluene to give 28.5 g of (−)-cis-4-(4-fluorophenyl)-3-hydroxymethyl-1-methylpiperidine, which is dissolved in thirty (30) ml of dry pyridine and fifty (50) ml of chloroform. The mixture is stirred at 10° C. and 24 g of benzenesulfonylchloride in 100 ml of chloroform is added dropwise. The mixture is allowed to stand at 0° C. for sixty (60) hours, and the reaction mixture then partitioned between 200 ml of toluene and 200 ml of water. The aqueous phase is extracted twice with thirty (30) ml of toluene. The combined toluene phase is evaporated to give 38.5 g of product, whereafter 3.5 g of sodium is dissolved in 250 ml methanol, twenty (20) g of p-methoxyphenol added thereto, and this mixture added to the toluene residue.

The mixture is refluxed for three (3) hours, whereafter the reaction mixture is partitioned between 200 ml of basic water and 200 ml of toluene. The aqueous phase is extracted twice with thirty (30) ml of toluene. The combined toluene phase is evaporated to give seventeen (17) g of oil. Seven (7) g of (−)-tartaric acid and 75 ml of water is added to fourteen (14) g of this oil. The mixture is stirred and a white substance precipitates. This compound is recrystallized from fifty (50) ml of water to yield two (2) grams of (+)-trans-4-(4-fluorophenyl)-3-[(4-methoxyphenoxy)methyl]-1-methyl-piperidine tartrate. M.p. 141.5°–142° C.

The base is isolated from the tartrate by partition between basic water and toluene to give 1.8 g of base. The title compound is then isolated by evaporation of the base in ethanol with concentrated hydrochloric acid. The residue is recrystallized from ethanol-ether (1:3) to yield 0.9 g of product. M.p. 180–182; $[\alpha]_D^{20}$ 73 (c=5 in ethanol).

EXAMPLE 9

(+)-trans-4-(4-fluorophenyl)-3-((4-methoxyphenoxy)-methyl)-piperidine acetate (FG 8035)

Fourteen (14) g of the free base of Example 8 is dissolved in 100 ml of dry toluene. The solution is stirred at 0° C. and ten (10) ml of chloroformic acid phenylester in thirty (30) ml of dry toluene is added dropwise over thirty (30) minutes. The mixture is left for twenty (20) hours at room temperature, whereafter a further ten (10) ml of chloroformic acid phenylester is added. The mixture is left for 72 hours, then 25 ml of toluene is added and the mixture extracted twice with 25 ml of 2N NaOH, once with 25 ml H$_2$O, twice with 25 ml 1N HCl, and once with ten (10) ml saturated aqueous NaCl. The toluene phase is dried with Na$_2$SO$_4$ drying agent and concentrated in vacuo to give 18.3 g of an oil, which is recrystallized from 96% ethanol to give 14.8 g of product as white crystals. This product is mixed with ten (10) g of potassium hydroxide and 100 ml of ethyleneglycol monomethyl ether. The mixture is stirred for four (4) hours at 130°–140° C. and is then concentrated in vacuo. The residue is partitioned between water and toluene. The toluene phase is dried with Na$_2$SO$_4$, filtered, and evaporated to give 2.2 g oil. Then 1.1 g of (−)-tartaric acid in 15 ml of water is added, whereupon 2.4 g of white crystals precipitate. The crystalline product is partitioned between basic water and ether. The organic phase is dried with Na$_2$SO$_4$ and acetic acid (100%) is added, whereafter 1.2 g of the title compound precipitates. M.p. 126°–127° C.; $[\alpha]_D^{20}$ 80° (C=5 in 99.9% ethanol).

EXAMPLE 10

Representative Pharmaceutical Compositions (a) Tablets suitable for oral administration which contain the following ingredients may be prepared by conventional tabletting techniques:

| Ingredient | Weight in mg |
| --- | --- |
| Active ingredient FG 8033 as the HCl or other salt | 10 |
| Calcium phosphate (CALCII PHOSPHAS) | 140 |
| Corn Starch (AMYLUM MAIDIS) | 36 |
| Polyvinylpyrrolidone (POLYVIDONUM) | 8 |
| Magnesium stearate (MAGNESII STEARAS) | 2 |
| Talcum | 2.5 |

(b) For suppositories, any usual suppository base may be employed for incorporation thereinto by usual procedure of the active ingredient, such as a polyethyleneglycol which is a solid at normal room temperature but which melts at or about body temperature.

(c) For parenteral (including subcutaneous) sterile solutions, the active ingredient together with conventional ingredients in usual amounts are employed, such as sodium chloride, sodium dihydrogen phosphate, disodium edetate (ethylenediaminetetraacetic acid disodium salt), benzyl alcohol, sodium hydroxide to adjust pH, and double-distilled water q.s., according to conventional procedure, such as filtration, aseptic filling into ampoules, and autoclaving for sterility.

Other suitable pharmaceutical compositions will be immediately apparent to one skilled in the art.

PHARMACOLOGY

The compounds of the invention have been found to exhibit an unpredictably favorable and highly advantageous degree of activity in the standard classic test for potentiation of 5-hydroxytryptophane-induced hypermotility in mice, which is indicative of serotonin, i.e., 5-hydroxytryptamine (5-HT), potentiation through inhibition of 5-HT uptake. (J. Buus Lassen, European Journal of Pharmacology 47, 351–358 (1978)). See also Squires in Acta Pharmacol. et Toxicol, 1972, 31 Suppl. 1,35 for a description of a further procedure for measurement of the same 5-HT uptake-inhibitory phenomenon. None of the compounds set forth in Table I were found to possess monoamineoxidase-inhibitory activity as evaluated by a lack or absence of ability to induce hyperactivity when administered in high doses, as during toxicity studies (J. Buus Lassen and R. F. Squires, Neuropharmacology 16, 485–488 (1977)). The compounds have moreover been determined to exhibit low toxicity, thereby producing an extremely favorable Therapeutic Index (TI) calculated as LD$_{50}$/ED$_{50}$.

I. POTENTIATION OF 5-HTP (5-HYDROXYTRYPTOPHANE) INDUCED HYPERMOTILITY IN MICE (Procedure 173)

Principle:

Parenteral treatment with 5-HTP increases the brain concentration of 5-HT and high doses decrease the concentration of NA and DA (References 1–4). Carlsson et al. have found that tricyclic thymoleptics with 5HT uptake-blocking activity induce behavioral changes in mice treated with 5-HTP (Reference 5). This behavior is characterized by continuous jerky locomotion, head movements from side to side, abduction of the hind limbs, tremor, and lordosis.

Using this test procedure, we have investigated the locomotor activity in mice after different doses of 5-HTP; 150 mg/kg producing a small decrease of motility, and 600 mg/kg increasing the activity. Administration of 5-HT-uptake blockers to mice pretreated with 5-HTP 150 mg/kg increases the activity significantly.

Pretreatment with the catecholamine synthesis inhibitor α-methyl-p-tyrosine does not influence this hyperactivity, whereas the central decarboxylase-inhibitor 3-hydroxybenzylhydrazine inhibited it significantly (Reference 6). Therefore, increased 5-HT in brain seems to be necessary for development of the abnormal behavior, but catecholamine release is probably not related to hyperactivity.

Measurement of the motility after administration of test drugs to 5-HTP-pretreated mice is therefore used as a test for 5-HT-potentiation, which most probably proceeds through an inhibition of 5-HT uptake.

Method:

Female mice of the NMRI strain weighing 20–22 g are used. The controls receive 5-HTP 150 mg/kg (15 ml/kg) i.p. (i.p.=intraperitoneally) and thirty (30) minutes later physiological saline (20 ml/kg) s.c. (s.c.=subcutaneously). The motility is measured by an Animex TM motimeter 45–75 minutes after 5-HTP administration. The test animals received test substance s.c. (20 ml/kg) instead of physiological saline. Five groups of two (2) mice are used for control and per dose of each test drug. the test substance is dosed according to the dose scale 1, 1.6, 2.5, 4, 6.3, and 10 mg/kg etc. The highest dose tested is about ten (10) percent of LD$_{50}$.

Result:

The activity of the test animals is compared to the activity of controls. The best straight line is fitted through the points in a coordinate system (abscissa log dose, ordinate log activity). Using this line, the dose in mg/kg increasing the activity to double the activity found with controls receiving 5-HTP alone is determined. The activity of controls is investigated in thirty (30) groups of two (2) mice. These results are used for determination of the ED dose.

Specificity of the test:

Compounds active in the test are scientifically considered to potentiate 5-HT-function by the inhibition of 5-HT uptake.

REFERENCES

1. Udenfriend et al., J. Biol. Chem. 1957, 224, 803–810.
2. Johnson et al., Proc. Soc. Exp. Biol. Med. 1968, 128, 509–512.
3. Fuxe et al., J. Pharm. Pharmacol. 1971, 23, 420–424.
4. Henning and Rubenson, Acta Pharmacol. et Toxicol. 1971, 29, 145–154.
5. Carlsson, Brain Res. 1969, 12, 456–460.
6. J. Buus Lassen, "Animal Pharm." Abstracts Uppsala 1972, 11.

II. ACUTE TOXICITY IN MICE (Procedure 001)

A variation of the procedure of J. Buus Lassen, et al. in European Journal of Pharmacology 32, 108–115 (1975) is employed. The test drug is administered s.c. in increasing doses to mice, four (4) animals at each dose level. The animals are observed for 24 hours and the lethality at that time is used for determining the $LD_{50}$, i.e., the dose which kills fifty (50) percent of the treated mice.

Results are expressed as $LD_{50} = \ldots$ mg/kg s.c.

The importance of such highly active 5-HT potentiators (5-HT uptake-inhibitors) is widely recognized by the medical, pharmacological, and pharmaceutical professions. For example, use of the compounds of the present invention to regulate 5-HT is of value in the treatment of any of numerous indications which are sensitive to changes in the central or peripheral nervous system serotonin (5-HT) balance or in the blood constituent serotonin balance, for example the blood platelet serotonin balance, as recognized by the following authors and publications:

A. Depression: D. L. Murphy et al., Psychopharmacology, pages 1235–1247 (1978).
B. Obesity: J. Smedegaard et al., International Journal of Obesity, 5, 377–378 (1981).
C. Myoclonus Syndromes: I. Magnussen et al., Acta Neurol. Scandinav. 66, 276–282 (1982).
D. Migraine: J. Dalsgaard-Nielsen et al., Acta Neurol. Scandinav. 66, 191–198 (1982).
E. Tension Headache: Ottar Sjaastad, Cephalalgia 3, 53–60 (1983).
F. Asthma: Philip Toennesen, Allergy 38, 283–285 (1983).
G. Antiinflammatory Activity: W. K. Khanna et al., Indian Journal of Experimental Biology 18, 607–611 (1980).
H. Activity against Memory Impairment: H. Weingartner, Science 221, 472–474 (1983).
I. Activity Against Dementia: I. Bergman et al., Psychopharmacology 80, 279–283 (1983).
J. Analgesic Activity: F. Johansson and L. Von Knorring, Pain 7, 69–78 (1979).
K. Phobic Anxiety: L. Evans et al., Prog. Neuro-Psychopharmacol. 4, 75–79 (1980).
L. Alcoholism: C. A. Naranjo, Meeting of the American Society for Clinical Pharmacology and Therapeutics, held in San Diego, Calif., USA (Mar. 9, 1983).
M. Treatment of Cataplexy: M. Schachter and J. D. Parkes, Journal of Neurology, Neurosurgery, and Psychiatry 43, 171–174 (1980).
N. Treatment of Narcolepsy: No author. The Lancet, page 845 (1975), I.

THE TABLE

The results of the 5-HT potentiation (or 5-HT uptake-inhibition) test 173 and the acute toxicity test 001, both performed subcutaneously and in the same test animal species, namely, mice, are presented in Table I, where the data is assembled not only for the compound of the invention FG 8033, but also for close relatives thereof, some of which are old and others of which have been newly-conceived and prepared for the first time, and all of which were tested in the form of a water-soluble salt.

From the Table it is apparent that the compound FG 8033 is remarkably and unpredictably superior in its 5-HT potentiation to the most structurally closely-related compounds evaluated, and even more remarkably and unpredictably superior to those most structurally closely-related compounds when considering its Therapeutic Index.

In direct comparison to its corresponding (+) trans isomer FG 8032 of Example 8, the compound FG 8033 is 46 times (4600%) as active in 5-HT potentiation and has a Therapeutic Index more than 47 times (4700%) as great.

Compared with FG 4962, the same (−), trans configuration of the corresponding des-p-fluoro compound, the 5-HT potentiation activity of FG 8033 is 7.6 times (760%) as great, and in Therapeutic Index more than 15 times or 1500% as great, whereas FG 8033 is superior to the corresponding (+), trans des-p-fluoro compound FG 4963 by a factor of 5.6 (560%) as to 5-HT potentiation, and greater than 5.97 times (597%) as to Therapeutic Index.

Other comparisons with FG 8033 are as follows:

| | FG 8033 is better by: | | | |
|---|---|---|---|---|
| | 5-HT Potentiation Factor | % | T.I. Factor | % |
| FG 8035 | 44 | 4400 | 33.33 | 3333 |
| FG 7006 | 40 | 4000 | 44.44 | 4444 |
| FG 4996 | 18 | 1800 | 57.14 | 5714 |
| FG 98-I | 2.6 | 260 | 1.74 | 174 |

The unpredictable magnitude of the advantageous characteristics or properties of the compound of the invention is apparent from the foregoing comparisons.

TABLE I

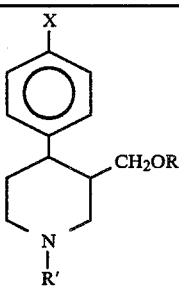

| FG # | m.p.°C. | salt | R' | R | X | (+), (−), rac | cis/trans | Test 173 | Test 001 | TI$^x$ | reference |
|---|---|---|---|---|---|---|---|---|---|---|---|
| 4932 | 234–5 | HBr | Me | A | H | rac | trans | 7.7 | 100 | 13 | * |
| 4963 | 191–3 | HCl | Me | A | H | (+) | trans | 2.8 | 375 | 134 | * |
| 4996 | 141–2 | HCl | H | A | H | (+) | trans | 9.0 | 125 | 14 | * |
| 4962 | 190–2 | HCl | Me | A | H | (−) | trans | 3.8 | 200 | 53 | * |
| 7006 | 142–3 | HCl | H | A | H | (−) | trans | 20.0 | 350 | 18 | * |
| 8032 | 180–2 | HCl | Me | A | 4-F | (+) | trans | 23.0 | 400 | 17 | NC Example 8 |
| 8035 | 126–7 | Acetate | H | A | 4-F | (+) | trans | 22.0 | 530 | 24 | NC Example 9 |
| 8033 | 178–9 | HCl | Me | A | 4-F | (−) | trans | 0.5 | 400 | 800 | CI Example 5 |
| 7080 | 165–8 | HCl | H | A | 4-F | (−) | trans | 1.0 | 1000 | 1000 | NC Example 6 |
| 7043 | 205–6 | HCl | Me | B | 4-F | (−) | trans | 4.0 | 250 | 63 | ** |
| 7051 | 136.5–137.5 | Maleate | H | B | 4-F | (−) | trans | 1.7 | 285 | 168 | ** |
| 98-I | 219–220 | HCl | Me | A | 4-F | rac | trans | 1.3 | 600 | 461 | NC*** |

*Compound synthesized according to U.S. Pat. No. 3,912,743
**Compound synthesized according to U.S. Pat. No. 4,007,196
***Recoverable from mother liquors of Examples 5 or 8 hereof.
NC New compound
CI Compound of the Present Invention
Test 173 is the inhibition of 5-HT uptake, or 5-HT potentiation, test
Test 001 is the acute toxicity test
TI is Therapeutic Index
$^x$001/173
A = para-methoxyphenyl
B = 3,4-methylenedioxyphenyl Ferroco D 6

Elemental analyses for the new fluorophenyl[methoxyphenoxymethyl]piperidine compounds synthesized according to the foregoing Examples are set forth in the following:

| | C | H | N | Cl |
|---|---|---|---|---|
| FG 8032 Analysis | | | | |
| Theoretical (Calc'd) | 65.66 | 6.89 | 3.83 | 9.69 |
| Found | 65.53 | 6.81 | 3.75 | 9.65 |
| FG 8035 Analysis | | | | |
| Theoretical (Calc'd) | 67.18 | 6.98 | 3.73 | |
| Found | 66.98 | 6.88 | 3.66 | |
| FG 8033 Analysis | | | | |
| Theoretical (Calc'd) | 65.66 | 6.89 | 3.83 | 9.69 |
| Found | 65.40 | 6.96 | 3.86 | 9.64 |
| FG 7080 Analysis | | | | |
| Theoretical (Calc'd) | 65.04 | 6.56 | 3.99 | 10.12 |
| Found | 65.05 | 6.79 | 4.00 | 10.11 |
| FG 98-I Analysis | | | | |
| Theoretical (Calc'd) | 65.66 | 6.89 | 3.83 | 9.69 |
| Found | 65.58 | 6.95 | 3.75 | 9.61 |

In conclusion, from the foregoing, it is apparent that the present invention provides a novel 5-HT potentiating 4-(4-fluorophenyl)-3-[(4-methoxyphenoxy)methyl]-1-methylpiperidine compound and acid addition salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. A compound selected from the group consisting of (−)-trans-4-(4-fluorophenyl)-3-[(4-methoxyphenoxy)-methyl]-1-methylpiperidine and a pharmaceutically-acceptable acid addition salt thereof.

2. A compound of claim 1, which is (−)-trans-4-(4-fluorophenyl)-3-[(4-methoxyphenoxy)methyl]-1-methylpiperidine hydrochloride.

3. A pharmaceutical composition suitable for use in 5-HT potentiation comprising an effective 5-HT potentiating amount of a compound of claim 1 together with a pharmaceutically-acceptable carrier or diluent.

4. A pharmaceutical composition suitable for use in 5-HT potentiation comprising an effective 5-HT potentiating amount of a compound of claim 2 together with a pharmaceutically-acceptable carrier or diluent.

5. A method of potentiating the 5-HT of a subject in need thereof comprising the step of administering to the said subject an effective 5-HT potentiating amount of a compound of claim 1.

6. A method of potentiating the 5-HT of a subject in need thereof comprising the step of administering to the said subject an effective 5-HT potentiating amount of a compound of claim 2.

7. A method of claim 5, wherein the compound is administered in the form of a pharmaceutical composition thereof, in which it is present together with a pharmaceutically-acceptable carrier or diluent.

8. A method of claim 6, wherein the compound is administered in the form of a pharmaceutical composition thereof, in which it is present together with a pharmaceutically-acceptable carrier or diluent.

UNITED STATES PATENT AND TRADEMARK OFFICE
CERTIFICATE OF CORRECTION

PATENT NO. : 4,593,036

DATED : June 3, 1986

INVENTOR(S) : Jorgen B. Lassen, Jorgen A. Christensen, Erling N. Petersen and John B. Hansen It is certified that error appears in the above-identified patent and that said Letters Patent is hereby corrected as shown below:

Title Page, [45] Date of Patent:; insert before "Jun. 3, 1986" an asterisk -- * --

Title Page [73] Assignee: "Soborg" should read -- Søborg --

Title Page, between the two paragraphs starting with "[73] Assignee:" and "[21] Appl. No.:" insert this separate paragraph;
-- [*] Notice: The portion of the term of this patent subsequent to April 29, 2003 has been disclaimed --

Title Page, Abstract, line 1; "-(4-florophenyl)-" should read -- -(4-fluorophenyl)- --

Col. 4, line 55; "-(4-fluorphenyl)-" should read -- -(4-fluorophenyl)- --

Col. 8, line 31; "5HT" should read -- 5-HT --

Col. 8, line 61; "TM" should read -- (TM) --

Col. 8, line 65; "the" (first occurrence) should read -- The --

Cols. 11&12, TABLE 1, column heading #11; "TI$^X$" should read -- TI$^®$ --

Cols. 11&12, TABLE 1, in the footnotes, line 9; "x001/173" should read -- ®001/173 --

Signed and Sealed this

Seventh Day of October, 1986

[SEAL]

Attest:

DONALD J. QUIGG

Attesting Officer

Commissioner of Patents and Trademarks